United States Patent [19]

Pedersen et al.

[11] Patent Number: 5,783,413
[45] Date of Patent: Jul. 21, 1998

[54] ENZYMATIC PROCESS FOR PRODUCING A DESIRED PROTEIN FROM AN AMINO TERMINAL EXTENDED PROTEIN

[75] Inventors: John Pedersen, Kokkedal; Conni Lauritzen, Rødovre; Mads Thorup Madsen, Copenhagen N., all of Denmark

[73] Assignee: Unizyme Laboratories A/S, Hørosholm, Denmark

[21] Appl. No.: 737,757

[22] PCT Filed: May 9, 1995

[86] PCT No.: PCT/DK95/00184

§ 371 Date: Feb. 5, 1997

§ 102(e) Date: Feb. 5, 1997

[87] PCT Pub. No.: WO95/30685

PCT Pub. Date: Nov. 16, 1995

[30] Foreign Application Priority Data

May 9, 1994 [DK] Denmark .................. 0533/94

[51] Int. Cl.$^6$ .................................................. C12P 21/06
[52] U.S. Cl. .................................................. 435/68.1
[58] Field of Search ...................................... 435/68.1

[56] References Cited

U.S. PATENT DOCUMENTS

| | | | |
|---|---|---|---|
| 4,543,329 | 9/1985 | Daum et al. | 435/69.1 |
| 4,745,051 | 5/1988 | Smith et al. | 435/69.51 |
| 5,013,662 | 5/1991 | Ben-Bassat et al. | 435/212 |
| 5,028,694 | 7/1991 | Mewman, Jr. et al. | 530/350 |
| 5,126,249 | 6/1992 | Becker et al. | 435/68.1 |
| 5,141,922 | 8/1992 | Krivi | 514/12 |

FOREIGN PATENT DOCUMENTS

| | | |
|---|---|---|
| 0 191 827 B1 | 8/1986 | European Pat. Off. . |
| 0 217 814 | 4/1987 | European Pat. Off. . |
| 0 489 711 A2 | 6/1992 | European Pat. Off. . |
| 91/15589 | 10/1991 | WIPO . |

OTHER PUBLICATIONS

Toshimoto, T. et al., *J. Biochem.* 113(1):67–73 (1993), pp. 67–73.

*Enzyme Nomenclature*, 1992, Recommendations of the Nomenclature Committee of the International Union of Biochemistry and Molecular Biology on the Nomenclature and Classification of Enzymes, pp. 199, 386.

Messer, M. et al., *Compt. Rend. Trav. Lab. Carlsberg* 35(1):1–24.

Metrione, R.M. et al., *Dipeptidyl Transferase (Cathepsin C)* 5(5):1597–1604, May 1966.

Yoshimoto, T. et al., *J. Biochem.* 104(1):93–97, 1988.

Yoshimoto, T. et al., *J. Biochem.* 105(3):412–416, 1989.

Shapiro, R. et al., *Analytical Biochemistry* 175:450–461, 1988.

*Primary Examiner*—Jon P. Weber
*Attorney, Agent, or Firm*—Darby & Darby

[57] ABSTRACT

An enzymatic process is presented for producing a desired protein from an amino terminal extended protein by reaction with one or more aminopeptidases, glutamine cyclotransferase and pyroglutamine aminopeptidase.

12 Claims, No Drawings

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

His  Ser  Gln  Gly  Thr  Phe  Thr  Ser
1                          5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single (D) TOPOLOGY: linear (i i) MOLECULE TYPE: peptide (i x) FEATURE:
    (A) NAME/KEY: Other
    (D) OTHER INFORMATION: Peptide attached to N terminus of
        glucagon.
    (A) NAME/KEY: Modified Base
    (D) OTHER INFORMATION: Xaa at position 1 represents
        des-His; Xaa at position 4 represents pGln (x i) SEQUENCE DESCRIPTION: SEQ ID NO:2:

Xaa  Ser  Gln  Xaa
 1

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:3:

Gly  Thr  Phe  Thr  Ser
 1                    5

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Other
        (D) OTHER INFORMATION: Peptide attached to N terminus of
            hTNFalpha.

(x i) SEQUENCE DESCRIPTION: SEQ ID NO:4:

Met  Arg  His  His  His  His  His  His  Gly  Arg  Gln
 1                  5                        10

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: Other (x i) SEQUENCE DESCRIPTION: SEQ ID NO:5:

CTGCAGCTAG  CCAGGTCAGA  TCATCTTCCC         30

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: Other ( x i ) SEQUENCE DESCRIPTION: SEQ ID NO:6:

GGTGAATTCG GATCCTTA 18

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other ( x i ) SEQUENCE DESCRIPTION: SEQ ID NO:7:

CATGCGTCAT CATCATCATC ATCATGGGCG 30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other ( x i ) SEQUENCE DESCRIPTION: SEQ ID NO:8:

CTAGCGCCCA TGATGATGAT GATGATGACG 30

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Val Arg Ser Ser Ser Arg Thr Pro Ser Asp
1               5                   10

( 2 ) INFORMATION FOR SEQ ID NO:10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Met Arg His His His His His His Arg Gln
1               5                   10

( 2 ) INFORMATION FOR SEQ ID NO:11:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Met Lys His Leu Ser Glu Ile Phe Glu Thr Met Lys Val Glu Leu Arg

```
  1               5               10              15
Gln
```

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: Peptide attached to N terminus of
            EGF.

(xi) SEQUENCE DESCRIPTION: SEQ ID NO:12:

```
Met Arg His His His His His His Gln
 1               5
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Asn Ser Asp Ser Glu
 1               5
```

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Met Lys His Leu Ser Glu Ile Phe Glu Thr Met Lys Val Glu Leu Arg
 1               5                   10                  15
Gln
```

(2) INFORMATION FOR SEQ ID NO:15:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (D) OTHER INFORMATION: Peptide attached to N terminus of
            TNFalpha.

(xi) SEQUENCE DESCRIPTION: SEQ ID NO:15:

```
Met Lys Glu Thr Ala Ala Ala Lys Phe Glu His Gln His Met Asn Ser
 1               5                   10                  15
```

```
Ser Arg Gln ( 2 ) INFORMATION FOR SEQ ID NO:16:

( i ) SEQUENCE CHARACTERISTICS:
                ( A ) LENGTH: 8 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:16:

Val Arg Ser Ser Ser Arg Thr Pro
 1           5

( 2 ) INFORMATION FOR SEQ ID NO:17:

( i ) SEQUENCE CHARACTERISTICS:
                ( A ) LENGTH: 12 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Other
                ( D ) OTHER INFORMATION: Peptide attached to N terminus of
                       TNFalpha.

( x i ) SEQUENCE DESCRIPTION: SEQ ID NO:17:

Met Arg Ser Ala Trp Arg His Pro Gln Phe Gly Gln
 1           5                    10
```

ENZYMATIC PROCESS FOR PRODUCING A DESIRED PROTEIN FROM AN AMINO TERMINAL EXTENDED PROTEIN

The invention relates to an enzymatic process for producing a desired protein from an amino terminal extended protein.

Over the past decade, the principle of a new protein purification technique has emerged as a result of recombinant DNA technology. DNA, encoding additional polypeptide or protein tags, is fused to the gene of interest. Expression of these gene fusions results in protein fusions which may be identified, analyzed and purified by techniques using the properties of the additional polypeptide tag. This has in certain cases eliminated the need for extensive screening and optimization procedures previously required for purification.

Polypeptide tags specifying a variety of different biospecific and biochemical interactions can be or have been utilized as the basis for fusion tag techniques. These include (1) entire enzymes with affinity for substrates or inhibitors; (2) peptide-binding proteins; (3) carbohydrate-binding proteins or domains; (4) biotin-binding domains; (5) antigenic epitopes with affinity for specific immobilized monoclonal antibodies; (6) charged amino acids for use in charge-based recovery methods; (7) polyhistidine residues for binding to metal chelates and subsequent recovery by immobilized metal affinity chromatography and (8) other polyamino acids with various binding specificities.

Provided that the added polypeptide tag can be effectively and specifically removed, this technology should find application in areas from basic research to industrial production. On a laboratory scale, the fusion tag technique should be a powerful and elegant tool for one-step recovery and purification of a large number of authentic recombinant proteins. On an industrial scale, the technology could be used in the recovery and purification of high-cost pharmaceuticals and other proteins prepared by using recombinant technology or other technology.

Unfortunately, the use of this protein purification principle has been very limited because of a major and serious drawback. It is often difficult, impossible or too expensive to remove the additional terminal sequence from the desired protein product. This is most often necessary to do in order to obtain the desired correct protein function, structure and other properties.

This is of the utmost importance when dealing with basic research covering e.g. function studies of proteins (enzymes, receptors, hormones, etc.).

It is also of the utmost importance when dealing with proteins for pharmaceutical use in which case it is essential to avoid undesired immunological and other response effects of the pharmaceutically active protein which therefore has to have the correct and natural structure, i.e. without any added polypeptide or single amino acid.

One solution to the problem has been to remove the added polypeptide tag by using relatively drastic conditions and chemical cleavage reagent, such as CNBr in 70% formic acid, or hydroxylamine treatment at basic pH. The methods have several major drawbacks which include the use of protein-destroying conditions and very toxic chemicals, this leading to high levels of unwanted degradation of the protein of interest and serious health problems for the personnel involved in the use of these techniques.

Another approach is to use so-called specific endoproteases. The blood clotting factor Xa has a proteolytic specificity for the tetra peptide sequence IleGluGlyArg and has been used to liberate different added sequences from different proteins. A sequence allowing a relatively specific cleavage by collagenase has also been proposed. Another sequence of five amino acids can be cleaved by the enzyme enterokinase.

Another example using this technique is known from DE 29 22 496 which partly corresponds to U.S. Pat. No. 4,543,329. This document discloses the preparation of proteins from C-terminal extended proteins. The protein is extended with 4 amino acids, where the extension is Pro-Xyz-Gly-Pro, and Xyz is any amino acid. The tetrapeptide is removed using the enzymes collagenase, an aminopeptidase and a proline aminopeptidase. No stop point is used for collagenase. Purification after removal is difficult, see the following. Further, proline is not the optimal amino acid as terminal, if it is desired to incorporate specific characteristics in the extension, because it reduces the movability of the extension. This means that it is more difficult to design an extension for a given purpose.

The above-mentioned types of endoproteases have thus in principle the ability to cleave at the C-terminal of their recognition sequence, resulting in liberation of the desired protein with the correct amino terminal.

The use of enzymatic methods using sequence specific endoproteases has, however, several major drawbacks. One of these is that the desired product should not contain the recognition sequence for the endoprotease used, because this will result in undesired degradation of the product. Furthermore, the selectivity is not always as precise as anticipated, because the enzyme can cleave at more or less homologous sequences in the desired product, or because the enzyme contains contaminating homologous endoproteases (which therefore are difficult to remove or inactivate), all of which will result in undesired modification or degradation of the protein product.

A further problem in connection with the use of sequence specific endoproteases is that the potentially useful enzymes are very often (extremely) expensive in use, especially when producing proteins for pharmaceutical use.

To overcome the problems associated with the chemical and endoproteolytic methods described above, it is in certain cases possible to use exoproteases to remove the amino(N)- or carboxy(C)-terminal extensions (amino- and carboxy-peptidases, respectively).

These enzymes remove an amino acid or a dipeptide from the unblocked N- or C-terminal of a peptide/protein. In order to fully control the removal of a terminal extension there must be a stop point at the N- or C-terminal, respectively, of the desired protein. If no such stop point exists, the result will be an unwanted further degradation of the protein.

An example of the use of an exopeptidase in connection with the removal of a terminal extension from a protein with a natural stop point is the use-of the enzyme dipeptidyl aminopeptidase I (DAP I; EC 3.4.14.1), see EP 217 814 and DK 166 687. DAP I is used in both cases to produce a desired protein containing an internal stop point within the protein itself.

DAP I is an enzyme which removes two amino acids, as a unit, from the N-terminal of a protein or polypeptide. Under appropriate conditions, dipeptide removal will commence and continue unless or until (1) the amino group of the N-terminal is blocked, (2) the site of removal is on either side of a proline, or (3) the N-terminal amino acid is lysine or arginine.

DAP I can thus be used to remove N-terminal extensions from a protein containing a proline as the second or third amino acid, or N-terminal lysine or arginine residue.

Another example of the use of an exopeptidase in connection with the removal of a terminal extension from a protein with a natural stop point is the use of the enzyme aeromonas aminopeptidase (AAP), which removes single amino acids from the N-terminal of a protein or polypeptide, cf. EP 489 711 and EP 191 827 disclosing removal of N-terminal residues by means of an aminopeptidase, e.g. AAP. Under appropriate conditions, amino acid removal will commence and continue unless or until (1) the amino group of the N-terminal is blocked, (2) the site of removal is on the N-terminal side of proline, or (3) the N-terminal amino acid is glutamic acid or aspartic acid.

Danish patent application no. 3245/89 corresponding to EP 348 780 discloses a process for preparing a protein from N-terminal extended protein, which is extended with at least a proline residue just in front of the protein. It is suggested that the process is useful when the extension contains more than one amino acid residue in front of the proline residue, but this is not possible. The enzyme used Aminopeptidase P, can only remove the amino acid residue just in front of the proline residue (Yoshimoto, T. et al., J. Biochem., Vol. 104, p. 93–97 (1988)).

This means that the method is only useful for removing N-terminal extension having only two amino acid residues and having the sequence Xaa-Pro (where Xaa is any amino acid residue).

DAP I and AAP may thus have some usefulness in the production of a desired recombinant protein from a precursor protein by constructing such precursor protein to contain a removable N-terminal extension, i.e. an extension which does not contain any of the above-mentioned stop points. Treatment of the precursor protein with either of the two enzymes may result in removal of the N-terminal extension.

This process, however, may be severely limited in its application, as dipeptide or amino acid removal by DAP I or AAP, respectively, will continue sequentially and unhindered until one of the aforedescribed termination sequences (stop point) is reached. Thus, the aminopeptidase approach should find limited use, being applicable generally only in those instances in which the N-terminal portion of the desired protein product is itself a DAP I or AAP stop point.

It is also known to remove N-terminal methionine from angiogenine by means of AAP followed by non-enzymatic cyclization, cf. Analytical Biochemistry 175, 450–461 (1988).

It has now surprisingly been discovered, however, that it is possible to design a generally removable N-terminal extension containing a removable stop point at the C-terminal of the extension, i.e. immediately before the N-terminal of the desired protein product, thus avoiding the need for an internal stop point in the desired protein product.

SUMMARY OF THE INVENTION

The present invention provides enzymatic processes for producing a desired protein from an aminoterminally extended version of the protein. Typically, the starting proteins have the formula NH2-A-Glutamine-Protein-COOH, wherein A represents one or more amino acids aminoterminal to a glutamine residue and protein represents the desired protein product. In practicing the invention, the aminoterminally extended protein is contacted either simultaneously or sequentially with: (a) one or more aminopeptidases; (b) glutamine cyclotransferase (GCT); and (c) pyroglutamine aminopeptidase (PGAP). The first aminopeptidase(s) catalyze(s) the removal of the amino acids aminoterminal to the glutamine; glutamine cyclotransferase then catalyzes the conversion of the glutamine to pyroglutamine; and, finally, pyroglutamine aminopeptidase catalyzes the removal of the pyroglutamine to produce the desired protein product.

Aminopeptidases that may be used in practicing the invention include without limitation dipeptidyl aminopeptidase I (DAP I), aeromonas aminopeptidase (AAP), aminopeptidase P (APP), and proline iminopeptidase (PIP). The aminoterminally extended starting protein may be reacted with the enzymes sequentially or simultaneously. The only requirement is that the reaction conditions used support the enzymatic activity of each enzyme. Schematically, a protein with such a removable N-terminal extension can be written as A-Glutamine-Protein           I wherein Protein is the desired protein, Glutamine is a glutamine residue attached directly to the amino terminal of the desired protein, and A is an amino acid sequence which is attached directly to the glutamine residue.

It has surprisingly been found that the desired protein can be obtained by using the process according to the invention which is defined in the characterizing portion of claim 1.

The term aminopeptidase, except for pyroglutamine aminopeptidase, as used in the specification covers usual aminopeptidases acting on amino acids with primary or secondary amino groups.

The protein I is preferably first reacted with one or more aminopeptidases and simultaneously with glutamine cyclotransferase and then with pyroglutamine aminopeptidase.

In some cases it is also possible to react the protein I with all enzymes simultaneously, e.g. in a mixture.

Further, it is in some cases possible first to react protein I with one or more aminopeptidases and then simultaneously with glutamine cyclotransferase and pyroglutamine aminopeptidase.

It is also possible to react protein I with one enzyme at a time.

It is preferred to use dipeptidyl aminopeptidase as aminopeptidase.

Good results are also obtained by using aeromonas aminopeptidase as aminopeptidase.

It is moreover possible to use more than one aminopeptidase, e.g. dipeptidyl aminopeptidase and aminopeptidase P or aeromonas aminopeptidase and aminopeptidase P.

The choice of aminopeptidase(s) depends on the amino acid sequence in A or vice versa. A is i.a. constructed according to the used aminopeptidase(s). The aminopeptidases are chosen according to their suitablity in connection with the specifically constructed extended protein.

The A-sequence can e.g. be an amino acid sequence designed to be removed by DAP I in the presence of the enzyme glutamine cyclotransferase (GCT), and it must therefore have an even number of amino acids where the first amino acid is different from lysine and arginine, all other uneven amino acids are different from proline, glutamine, lysine and arginine, and all even amino acids are different from proline.

A desired protein with glutamine as the only N-terminal extension left can be cyclizised to the pyroglutamine by the enzyme (GCT), i.e. it is converted to an amino acid with a blocked amino group, and aminopeptidases cannot proceed through this amino acid residue.

Then, by using one or more aminopeptidases together with a surplus of GCT in an enzymatic reaction containing the N-terminal extended protein product, GCT will cyclizise the glutamine residue to a pyroglutamine residue, as soon as the aminopeptidases, such as DAP I or AAP, have removed all the amino acids before the glutamine residue. This cyclization reaction will thus result in a blocked N-terminal immediately before the desired protein product, and the reaction catalyzed by the aminopeptidase(s) will not proceed any further.

If the desired protein has the amino terminal sequence Xaa-Pro-, there is no need for a simultaneous reaction with DAP I and GCT, because the DAP I reaction will always stop immediately before the glutamine residue due to the proline residue in the desired protein.

This means that the DAP I treatment can be performed alone, and GCT can then be added to the reaction mixture. Furthermore, there is no need for using a surplus of GCT.

For the same reason as above, it is possible to perform all three enzymatic reactions at the same time by using both DAP I, GCT and PGAP in the same reaction mixture.

The resulting N-terminal pyroglutamine residue can be effectively and selectively removed by the enzyme pyroglutamine aminopeptidase (PGAP; EC. 3.4.11.8), resulting in the desired protein product without any N-terminal extension and with the correct and desired N-terminal amino acid.

Since no enzyme reactions can be expected to lead to 100% conversion, the PGAP catalyzed removal of the pyroglutamine residue is very advantageous. This is because a protein with blocked amino terminal, i.e. pyroglutamine, has a neutral amino acid at the amino terminal, and it will therefore act as a protein with an amino terminal amino acid having a free amino group and a negatively charged side chain, i.e. glutamic acid and asparagine. Then, as the pyroglutamine removal proceeds, the PGAP catalyzed removal of the amino terminal pyroglutamine residue from the desired protein results in a change in the total charge. This change then enables analytical and preparative separation by ion exchange chromatography and electrophoresis of the desired protein from the pyroglutamine extended protein. This is of the utmost importance in order to follow the enzymatic conversion and in order to isolate the desired protein without any pyroglutamine extension.

If the A-sequence contains one or more proline residues, the enzymatic removal will stop one or two amino acids from the first proline residue.

However, it has surprisingly been found that if the A-sequence contains either a single proline residue or two or more adjacent proline residues—or a mixture of either single proline residues and/or two or more adjacent proline residues separated by an even number of amino acids—and no proline residue as the C-terminal amino acid of the A-sequence—and an uneven number of amino acids before the first proline residue, the entire A-sequence can be removed in a reaction mixture with a combination of GCT, DAP I, and the well-examined enzyme aminopeptidase P (APP), which is known to selectively remove an amino acid from the N-terminal of an amino acid sequence, if the amino acid is followed by a proline residue. Furthermore, if the A-sequence contains either a single proline residue or two or more adjacent proline residues, or a mixture of either single proline residues and/or two or more adjacent proline residues separated by an uneven number of amino acids, and a proline residue as the C-terminal amino acid of the A-sequence, and an uneven number of amino acids before the first proline residue, the entire A-sequence can be removed in a reaction mixture with a combination of GCT, DAP I, APP, and the well-examined enzyme proline iminopeptidase (PIP) which is known to selectively remove an N-terminal proline residue from an amino acid sequence.

Further, it has surprisingly been found that using AAP together with a surplus of GCT in an enzymatic reaction containing the N-terminal extended protein product, GCT will cyclizise the glutamine residue to a pyroglutamine residue, as soon as AAP has removed all the amino acids before the glutamine residue. This cyclization reaction will thus result in a blocked N-terminal immediately before the desired protein product, and the reaction catalyzed by the aminopeptidase(s) will not proceed any further.

By using exopeptidases as described in this invention, undesired and unspecific internal cleavage of the desired protein product can be fully avoided.

The enzymes used in the present invention can easily and cheaply be produced in a highly purified form.

EXPERIMENTAL DETAILS

Materials and Methods

DAP I was prepared from turkey liver essentially according to Metrione, R. M. et al. Biochemistry 5, 1597–1604 (1966). The purification procedure included the following steps: Extraction autolysis, ammonium sulfate precipitation, gel filtration on Sephacryl® S-300 HR, desalting on Sephadex® G 25 F, and anion exchange chromatography on DEAE-Sepharose® FF. Purified DAP I was stored at −18° C. in 2 mM sodiumphosphase buffer, 150 mM NaCl 2 mM cysteamine, 50% glycerol, pH 6.8.

GCT was prepared from crude papaya latex essentially according to Messer, M. and M. Ottesen, Compt. Rend. Trav. Lab. Carlsberg, 35, 1–24 (1965), except that CM-Sepharose® FF replaced CM-Sephadex® employed by Messer and Ottesen. Purified GCT was stored at −18° C. in 4 mM sodiumphosphate buffer, 20 mM NaCl, 50% glycerol, pH 7.0.

PGAP was prepared from extracts of $E.$ $coli$ DH1, harbouring the PGAP expression plasmid pBPG 1, described by Yoshimoto, T. et al., J. Biochem. 113, 67–73 (1993). The purification procedure included the following steps: Centrifugation, followed by hydrophobic interaction chromatography on phenyl-Sepharose® FF and buffer exchange on Sephadex® G 25 F. Purified PGAP was stored at −18° C. in 6 mM Tris-Cl, 40 mM NaCl, 2 mM EDTA, 2 mM cysteamine, 50% glycerol, pH 8.0.

APP was prepared from extracts of E. Coli DH1, harbouring an APP expression plasmid similar to pAPP4, described by Yoshimoto, T. et al, J. Biochem. 105, 412–416 (1989). The purification procedure included the following steps: Centrifugation, ammonium sulphate fractionation, followed by anion exchange chromatography of DEAE-Sepharose FF and gel filtration of Sephacryl S-300 HR. Purified PGAP was stored at −18° C. in 6 mM Tris-Cl, 40 mM NaCl, 0.1 mM $Mn_2Cl$, 50% glycerol, pH 7.5.

The invention is further defined by reference to the following examples.

EXAMPLE 1

Removal of His-Ser-Gln from Glucagon

| | |
|---|---|
| Glucagon | 5 mg/ml in 0.01 HCl |
| DAP I (20 U/ml) | 100 µl are mixed with 900 µl 100 mM dithiothreitol |
| GCT (375 U/ml) | 100 µl are mixed with 900 µl $H_2O$ |
| PGAP (20 U/ml) | 100 µl are mixed with 100 µl $H_2O$ |
| Chicken cystatin | 1 mg/ml in 10 mM Tris ®-Cl, 50% glycerol, pH 7.5 |

Step 1

Removal of $His^1$-$Ser^2$ from glucagon and conversion of $Gln^3$ to pGln by DAPI/GCT 400 µl glucagon (2 mg; 0.57 µmol) with the amino terminal $His^1$-$Ser^2$-$Gln^3$-$Gly^4$-$Thr^5$-$Phe^6$-$Thr^7$-$Ser^8$ SEQ ID NO: 1 are mixed with 100 μl DAP I (0.2 unit), 80 μl GCT (3 units) and 1420 μl 100 mM sodium phosphate buffer, pH 7.0, and then incubated at 37° C. After 20 min, 1500 μl are taken out in 710 μl H$_2$O and 40 μl chicken cystatin (40 μg) (Sigma) and incubated for 30 min at 23° C. to inactivate DAP I activity, whereafter 1000 μl are desalted on a Sephadex® G 25 column (NAP 10) equilibrated with 10 mM sodium phosphate buffer, pH 7.0 (sample A).

Step 2

Removal of pGln from des-His$^1$-Ser$^2$-Gln$^3$[pGln$^3$]-glucagon SEQ ID NO: 2 with PGAP Another 1200 μl of the chicken cystatin inactivated reaction mixture are mixed with 20 μl PGAP (0.2 unit), incubated at 37° C., and after 5 min 1000 μl are desalted as above (sample B).

Samples A and B were subjected to amino terminal sequence determination on an "Applied Biosystems 477 A Protein Sequencer". No sequence could be determined for sample A, which means that it has a blocked amino terminal, i.e. pGln. Sample B, however, had the amino terminal sequence Gly-Thr-Phe-Thr-Ser, SEQ ID NO: 3 which means that PGAP has removed the amino terminal pGln residue.

Thus, by the sequential treatment with DAP I/GCT and PGAP, the sequence His-Ser-Gln has been specifically removed from glucagon.

EXAMPLE 2

Production of HisTag2-hTNFα

This example describes in details the plasmid construction used to produce His-tagged hTNFα in *E. coli*.

Plasmid DNA, BBG18, (British Biotechnology) carrying a modified cDNA sequence encoding the mature Human Tumour Necrosis Factor α (hTNFα) N-terminal extended with methionine is used as template in a Polymerase Chain Reaction (PCR) with the use of the synthetic oligonucleotides SEQ 5$^{(1)}$ and SEQ 6 as primers. The amplified DNA product is the sequence encoding hTNFα N-terminal extended with glutamine instead of methionine and with a NheI restriction site at the 5' end of the glutamine codon. The amplified DNA is subcloned as a NheI-EcoRI fragment into the NheI/EcoRI restriction sites of the *E. coli* expression vector, pTrcHis (Invitrogen Corporated) resulting in the plasmid pCLU7. By replacement of the small his-tag encoding NcoI-NheI fragment on pCLU7 with a synthetic linker (oligonucleotides SEQ 7 and SEQ 8) encoding a modified his-tag designed for optimal expression and subsequent removal by the process of the invention, the plasmid pCLU14 is obtained. In order to bring the hTNFα gene in frame with the his-tag, pCLU14 is digested with NheI followed by a Mung Bean nuclease treatment for removal of single stranded extensions to obtain blunt ends. Finally, the DNA is religated to give the expression plasmid pCLU15-1. pCLU15-1 encodes hTNFα N-terminally fused to the extension peptide, Met-Arg-His-His-His-His-His-His-Gly-Arg-Gln-hTNFα SEQ ID NO: 4

$^{(1)}$ DNA oligonucleotides

SEQ 5: CTG CAG CTA CCC AGG TCA GAT CAT CTT CGC

SEQ 6: GGT GAA TTC GGA TCC TTA

SEQ 7: CAT GCG TCA TCA TCA TCA TCA TCA TGG GCG

SEQ 8: CTA GCG CCC ATG ATG ATG ATG ATG ATG ACG

In parallel, other variants of histidine purification tags and other purification tags for affinity chromatography are fused to the hTNFα gene by replacement of the NcoI-NheI fragment of pCLU7 by synthetic linkers.

Likewise, the gene encoding the Human Epidermal Growth Factor (hEGF) obtained from Invitrogen Corporation on the plasmid BBG7 is modified by PCR and incorporated in the pCLU14 plasmid replacing the hTNFα gene to give the expression plasmid pCLU17 encoding hEGF fused to the his-tag.

N-terminal extended hTNFα is produced in *E. coli* strain TOP10 (Invitrogen Corporated) transformed with expression plasmids. Cells are cultured in medium scale (4–8×0.5 litre) in SOB +ampicillin at 37° C. Gene expression is induced by addition of IPTG at OD$_{600}$=0.6. Cells are harvested by centrifugation after another 4 hours of incubation at 37° C.

EXAMPLE 3

Generation of authentic TNFα from Met-Arg-6xHis-Gly-Arg-Gln-TNFα (HisTag2-TNFα SEQ ID NO:4)

(HisTag2-TNFα) is expressed in *E. coli* as described in example 2 and purified by metal chelate chromatography on an Ni$^{2+}$-NTA column:

| | |
|---|---|
| Matrix | Ni$^{2+}$-NTA *Agarose* (Qiagen) |
| Column | 2 cm$^2$ × 5 cm |
| Buffer A | 50 mM Tris-Cl, 300 mM NaCl, pH 8.0 |
| Buffer B | 25 mM Bis-Tris-Cl, 300 mM NaCl, 10% glycerol, pH 6.0 |
| Buffer C | 25 mM Bis-Tris-Cl, 300 mM NaCl, 10% glycerol, 1.0 M imidazole, pH 6.0 |
| Sample | 10 ml *E. coli* extract in Buffer A |
| Flow rate | 60 ml per hour |
| Fractions | 2 ml (2 minutes) |
| Elution | 1. Sample (10 ml) |
| | 2. 12 ml Buffer A |
| | 3. 12 ml Buffer B |
| | 4. 75 ml gradient from Buffer B to Buffer C |
| | 5. 25 ml Buffer C |

To remove the purification tag comprising 11 amino acids, HisTag2-TNFα (0.5 mg/ml; pH6.0) is first treated with DAP I (50 mU/mg) and GCT (1500 mU/mg) at 37° C. for 30 minutes. The reaction is followed by SDS-PAGE (data not shown). It is seen that a small amount (about 15%) of unconverted HisTag2-TNFα is still present after 30 minutes, and, prolonged treatment with DAP I and GCT does not change that. The reason for this could be either the presence of N-terminal terminal formyl methionine in a percentage of the protein or due to the known oligomeric structure of TNFα. After removal of the unconverted HisTag2-TNFα on a Ni-NTA column, the resultant product is subjected to N-terminal determination. No sequence is detected indicating the presence of pyroglutamine residue at the N-terminal of TNFα. To avoid uncontrolled further cleavage into TNFα, DAP I is inactivated before treatment with PGAP. This is done by treatment at pH 10.5 for 10 min, following by adjusting pH to 8.0. The presumed PyroGln-TNFα (at 0.5 mg/ml and pH 8.0) is then treated for 60 min at 37° C. with PGAP (500 mU/mg). PGAP is removed from the reaction mixture by IE-HPLC fractionation on MonoQ at pH 7.0, and the purified product is subjected to N-terminal sequence determination. The sequence is Val-Arg-Ser-Ser-Ser-Arg-Thr-Pro-Ser-Asp SEQ ID NO: 9 in agreement with the N-terminal sequence of TNFα.

EXAMPLE 4

Generation of authentic TNFα from Met-Arg-6xHis- Ara-Gln-TNFα(HisTag3-TNFα SEQ ID NO: 10)

(HisTag3-TNFα) is expressed in *E. coli* as described in example 2 for HisTag2-TNFα and purified by metal chelate chromatography on an Ni²⁺-NTA column as described in example 3 for HisTag2-TNFα. To simplify the method and secure optimal removal of enzymes, a procedure is developed, which uses biotinylated DAP I and PGAP. These enzymes can be removed on streptavidin or Avidin matrices. Furthermore, GCT have affinity for Ni-NTA-Agarose and can therefore be removed simultaneously with unconverted HisTag protein. Alternatively, GCT can easily be removed on a cation exchanger at pH 7.5 because GCT has an isoelectric point around 9.0.

To remove the purification tag comprising 9 amino acids, HisTag3-TNFα (2.2 mg at 0.5 mg/ml; 4.5 ml) is treated with Biotin-DAP I (25 mu/mg) and GCT (750 mu/mg) for 30 min (Sample A). To remove Biotin-DAP I, sample A is passed through a 0.75 ml Streptavidin column (Sample B), and unconverted HisTag3-TNFα and GCT are removed on a Ni-NTA-Agarose column. (Sample C, PyroGln-TNFα). After removal of the unconverted HisTag3-TNFα, the resultant product is subjected to N-terminal determination. No sequence is detected indicating the presence of pyroglutamine residue at the N-terminal of TNFα.

To remove pyroGln 1.4 mg (6 ml) PyroGln-TNFα is treated with Biotin-PGAP (400 mu/mg for 18 h at 7° C.; Sample D). To remove Biotin-PGAP, sample D is passed through a 0.75 ml Streptavidin column (Sample E). The purified product is subjected to N-terminal sequence determination. The sequence is Val-Arg-Ser-Ser-Ser-Arg-Thr-Pro-Ser-Asp SEQ ID NO: 9 in agreement with the N-terminal sequence of TNFα.

EXAMPLE 5

Generation of authentic TNFα from Met-Lys-His-Leu-Ser-Glu- Ile-Phe-Glu-Thr-Met-Lys-Val-Glu-Leu-Ara-Gln-TNFα(BiotinTa91 -TNFα SEQ ID NO: 11)

BiotinTag1-TNFα is expressed in *E. coli* essentially as described in example 2 for HisTag2-TNFα and purified by affinity chromatography on an Immobilized Monomeric Avidin Agarose gel:

| | |
|---|---|
| Matrix | Immobilized Monomeric *Avidin Agarose* (Pierce) |
| Column | 0.8 cm² × 6 cm |
| Buffer A | 100 mM sodium phosphate Na₃PO₄, 150 mM NaCl, pH 7.5 |
| Buffer B | 100 mM sodium phosphate Na₃PO₄, 150 mM NaCl, 2 mM D-Biotin, pH 7.5 |
| Sample | 10 ml *E. coli* extract in Buffer A |
| Flow rate | 15 ml per hour |
| Fractions | 1 ml (4 minutes) |
| Elution | 1. Sample (10 ml) |
| | 2. 20 ml Buffer A |
| | 3. 40 ml Buffer B |

To remove the purification tag comprising 17 amino acids, BiotinTag1-TNFα dialyzed against 20 mM sodium phosphate Na₃PO₄, 50 mM NaCl, pH 6.2 (2 mg at 0.5 mg/ml; 2 ml) is treated with Biotin-DAP I (100 mU/mg) and GCT (3000 mU/mg) for 60 min (Sample A). To remove Biotin-DAP I, unconverted BiotinTag1-TNFα and GCT, sample A is adjusted to pH 7.5 and passed through a 1.5 ml Avidin/0.5 mlCM-Sepharose column equilibrated with 20 mM sodium phosphate Na₃PO₄, 50 mM NaCl, pH 7.5 (Sample B, PyroGln-TNFα). The resultant product is subjected to N-terminal determination. No sequence is detected indicating the presence of pyroglutamine residue at the N-terminal of TNFα.

To remove pyroGln, 1.1 mg (4 ml) PyroGln-TNFα is treated with Biotin-PGAP (500 mU/mg for 18 h at 7° C.; Sample C). To remove Biotin-PGAP, sample C is passed through a 0.75 ml Avidin column (Sample D). The purified product is subjected to N-terminal sequence determination. The sequence is Val-Arg-Ser-Ser-Ser-Arg-Thr-Pro-Ser-Asp SEQ ID NO: 9 in agreement with the N-terminal sequence of TNFα.

EXAMPLE 6

Generation of authentic EGF from Met-Arg-6xHisGln-EGF SEQ ID NO: 12 (HisTag3-EGF)

(HisTag3-EGF) is expressed in *E. coli* essentially as described in example 2 for HisTag2-TNF and purified by metal chelate chromatography on an Ni²⁺-NTA column as described in example 3 for HisTag2-TNFα.

To remove the purification tag comprising 9 amino acids, HisTag3-EGF (1.3 mg at 0.5 mg/ml) is treated with Biotin-DAP I (50 mU/mg) and GCT (1500 mU/mg) for 30 min (Sample A). To remove Biotin-DAP I, sample A is passed through a 0.75 ml Avidin column (Sample B,) and unconverted HisTag3-EGF and GCT is removed on a Ni-NTA-Agarose column. (Sample C, PyroGln-EGF). After removal of the unconverted HisTag2-EGF, the resultant product is subjected to N-terminal determination. No sequence is detected indicating the presence of pyroglutamine residue at the N-terminal of EGF.

To remove pyroGln, 1.0 mg (6 ml) PyroGln-EGF is treated with Biotin-PGAP (1000 mU/mg for 18 h at 7° C.; Sample D). To remove Biotin-PGAP, sample D is passed through a 0.75 ml Avidin column (Sample E). The purified product is subjected to N-terminal sequence determination. The sequence is Asn-Ser-Asp-Ser-Glu SEQ ID NO: 13 in agreement with the N-terminal sequence of EGF.

EXAMPLE 7

Generation of authentic EGF from Met-Lys-HisLeu-Ser-Glu-Ile-Phe-Glu-Thr-Met-Lys-Val-Glu-Leu-Ara-Gln-EGF (BiotinTag1-EGF SEQ ID NO: 14)

BiotinTag1-EGF is expressed in *E. coli* essentially as described in example 2 for HisTag2-TNFα and purified by affinity chromatography on an Immobilized Monomeric Avidin Agarose gel (Pierce) essentially as described for BiotinTag1-TNFα in example 5.

To remove the purification tag comprising 17 amino acids, BiotinTag1-EGF dialyzed against 20 mM Na₃PO₄, 50 mM NaCl, pH 6.2 (2.6 mg at 0.5 mg/ml; 2 ml) is treated with Biotin-DAP I (250 mU/mg) and GCT (7500 mU/mg) for 60 min (Sample A). To remove Biotin-DAP I, unconverted BiotinTag1-EGF and GCT, sample A is adjusted to pH 7.5 and passed through a 1.5 ml Avidin/0.5 mlCM-Sepharose column equilibrated with 20 mM sodium phosphate Na₃PO₄, 50 mM NaCl, pH 7.5 (Sample B,-PyroGln-EGF). The resultant product is subjected to N-terminal determination. No sequence is detected indicating the presence of pyroglutamine residue at the N-terminal of EGF.

To remove pyroGln, 2.1 mg (4 ml) PyroGln-EGF is treated with Biotin-PGAP (1000 mU/mg for 18 h at 7° C.; Sample C). To remove Biotin-PGAP, sample C is passed through a 0.75 ml Avidin column (Sample D). The purified product is subjected to N-terminal sequence determination. The sequence is Asn-Ser-Asp-Ser-Glu SEQ ID NO: 13 in agreement with the N-terminal sequence of EGF.

EXAMPLE 8

Generation of authentic TNFα from Met-Lys-Glu-Thr-Ala-Ala-Ala-Lys-Phe-Glu-His-Gln-His-Met-Asn-Ser-Ser-Arg-Gln-TNFαSEQ ID NO: 15(S-Tag1-TNFα)

(S-Tag1-TNFα) is expressed in *E. coli* essentially as described in example 2 for HisTag2-TNF and purified by affinity chromatography on immobilized S-protein (S-Protein Agarose Novagen) at 4° C.: 10 ml E. coli extract containing S-Tagl-TNFα in 25 mM sodium phosphate Na₃PO₄, pH 7.5, is added to 1.65 ml S-Protein Agarose equilibrated with 25 mM sodium phosphate Na₃PO₄, pH 7.5, and the mixture is incubated for one hour at 4° C., with mixing each 10 min. The mixture is then packed in a small open plastic column (at 4 ° C.) and after the gel has settled, it is washed with 5 ml 25 mM sodium phosphate Na₃PO₄, pH 7.5. The column is closed at the bottom and heated to 37° C. in a water bath, whereafter the S-Tagl-TNFα is eluted with 2.5 ml 25 mM sodium phosphate Na₃PO₄, 500 mM NaCl, pH 7.5, preheated to 37° C.

To remove the purification tag comprising 19 amino acids, S-Tagl-TNFα in 20 mM sodium phosphate Na₃/PO₄, 50 mM NaCl, pH 6.2, (0.5 mg in 2.2ml) is treated with Biotin-DAP I (125 mU/mg) and GCT (2500 mU/mg) for 60 min (Sample A). To remove Biotin-DAP I and GCT, the sample is passed through a mixed 1.5 ml Avidin Agarose/0.5 ml CM-Sepharose column equilibrated with 20 mM sodium phosphate Na₃PO₄, 50 mM NaCl, pH 7.5, (Sample B), and unconverted S-Tagl-TNFα is removed on a 0.5 ml S-Protein Agarose column equilibrated with 20 mM sodium phosphate Na₃PO₄, 50 mM NaCl, pH 7.5, (4° C.). (Sample C, PyroGln-TNFα). The resultant product is subjected to N-terminal determination. No sequence is detected indicating the presence of pyroglutamine residue at the N-terminal of TNFα.

To remove pyroGln, 0.4 mg (7.5 ml) PyroGln-TNFα is treated with Biotin-PGAP (800 mU/mg for 16 h at 7° C.; Sample D). To remove Biotin-PGAP, sample D is passed through a 0.75 ml Avidin column equilibrated with 20 mM sodium phosphate Na₃PO4, 50 mM NaCl, pH 7.5, (Sample E). The purified product is subjected to N-terminal sequence determination. The sequence is Val-Arg-Ser-Ser-Ser-Arg-Thr-Pro SEQ ID NO: 16 in agreement with the N-terminal sequence of TNFα.

Example 9

Generation of authentic TNFα from Met-Ara-Ser-Ala-Trp-Arq-His-Pro-Gln-Phe-Gly-Gln-TNFα (StrepTag1-TNFα SEQ ID NO: 17)

(StrepTagl-TNFα) is expressed in E. Coli as described in example 2 for HisTag2-TNFα and purified by affinity chromatography on Streptavidin Agarose:

| | |
|---|---|
| Matrix | Streptavidin Agarose (Sigma) |
| Column | 0.8 cm² × 6 cm |
| Buffer A | 100 mM Na₃PO₄, 150 mM NaCl, pH 7.5 |
| Buffer B | 100 mM Na₃PO₄, 150 mM NaCl, 2 mM Imino-Biotin, pH 7.5 |
| Sample | 10 ml E. Coli extract in Buffer A |
| Flow rate | 15 ml per hour |
| Fractions | 1 ml (4 minutes) |
| Elution | 1. Sample (10 ml) |
| | 2. 20 ml Buffer A |
| | 3. 40 ml Buffer B |

To remove the purification tag comprising 12 amino acids, StrepTagl-TNFα in 100 mM Na₃PO₄, 150 mM NaCl, pH 6.2, (2.8 mg in 2.8 ml) is treated with Biotin-DAP I (200 mU/mg), Biotin-APP (Biotinylated AAP; 75 mU/mg) and GCT (2500 mU/mg) for 90 min at 37° C. (Sample A). To remove Biotin-DAP I, Biotin-APP, unconverted StrepTagl-TNFα and GCT, the sample is adjusted to pH 7.5 passed through a mixed 1.5 ml Streptavidin Agarose/0.5 ml CM-Sepharose column equilibrated with 20 mM Na₃PO₄, 50 mM NaCl, pH 7.5, (Sample B, PyroGln-TNFα). The resultant product is subjected to N-terminal determination. No sequence is detected indicating the presence of pyroglutamine residue at the N-terminal of TNFα.

To remove pyroGln, 0.4 mg (7.5 ml) PyroGln-TNFα is treated with Biotin-PGAP (600 mU/mg for 16 h at 7° C.; Sample C). To remove Biotin-PGAP, sample D is passed through a 0.75 ml Avidin column equilibrated with 20 mM Na₃PO₄, 50 mM NaCl, pH 7.5 (Sample D) The purified product is subjected to N-terminal sequence determination. The sequence is Val-Arg-Ser-Ser-Ser-Arg-Thr-Pro SEQ ID NO: 16 in agreement with the N-terminal sequence of TNFα.

We claim:

1. An enzymatic process for producing a desired protein, wherein an amino terminally extended protein of the formula $$\text{A-Glutamine-Protein} \qquad \text{I}$$

wherein Protein is the desired protein, Glutamine is a glutamine residue attached directly to the amino terminal of the desired protein, and A is an amino acid sequence which is attached directly to the glutamine residue, is reacted with (i) at least one aminopeptidase other than pyroglutamine aminopeptidase, (ii) glutamine cyclotransferase and (iii) pyroglutamine aminopeptidase to produce said desired protein.

2. The process of claim 1, wherein the protein of formula I is (I) first reacted simultaneously with (i) at least one aminopeptidase and glutamine cyclotransferase and (ii) then with pyroglutamine aminopeptidase.

3. The process of claim 1, wherein the protein of formula I is reacted simultaneously with all of at least one aminopeptidase, glutamine cyclotransferase and pyroglutamine aminopeptidase.

4. The process of claim 1, wherein the protein of formula I is (I) first reacted with at least one aminopeptidase and (ii) then reacted simultaneously with glutamine cyclotransferase and pyroglutamine aminopeptidase.

5. The process of claim 1, wherein the protein of formula I is (I) first reacted with at least one aminopeptidase, (ii) then reacted with glutamine cyclotransferase and (iii) reacted finally with pyroglutamine aminopeptidase.

6. The process of claim 1, wherein A has an even number of amino acids, where the first amino acid, as seen from the amino terminal, is different from glutamine, lysine and arginine, all other uneven amino acids are different from glutamine, proline, lysine and arginine, and all even amino acids are different from proline when dipeptidyl aminopeptidase is used as aminopeptidase.

7. The process of claim 1, wherein the first amino acid, as seen from the amino terminal in A, is different from glutamine, glutamic acid and aspartic acid, and all other amino acids are different from proline, glutamine, glutamic acid and aspartic acid when aeromonas aminopeptidase is used as aminopeptidase.

8. The process of claim 1, wherein A in formula I is selected from the group consisting of:

(i) A in formula I comprising at least one proline as a single proline residue (ii) A in formula I comprising at least one set of two or more adjacent proline residues; and (iii) a mixture of single proline residues and two or more adjacent proline residues separated by an even number of amino acids, when dipeptidyl aminopeptidase and aminopeptidase P are used as aminopeptidases, provided that:

(a) the C-terminal amino acid residue of the A-sequence is not a proline residue, (b) there is an uneven number of amino acids before and after the first and last occurring proline (c) any amino acid immediately before a proline residue is different from glutamine, (d) all uneven amino acids except the last uneven amino acid before the first occurring proline residue, as seen from the amino terminal, are different from glutamine, lysine and arginine, and (e) all amino acids following proline residue as an uneven amino acid except the last uneven amino acid, where proline is the first amino acid, are different from glutamine, lysine and arginine.

9. The process of claim 1, wherein A contains at least one proline where all amino acids are different from glutamine, glutamic acid and aspartic acid when aeromonas aminopeptidase and aminopeptidase P are used as aminopeptidases.

10. An enzymatic process for producing a desired protein product, which comprises:

(i) providing an aminoterminally extended protein having the formula

A-Glutamine-Protein, wherein A represents one or more amino acids aminoterminal to said glutamine residue and protein represents the desired protein product carboxyterminal to said glutamine residue; and (ii) contacting said aminoterminally extended protein simultaneously or sequentially with:

(a) at least one aminopeptidase other than pyroglutamine aminopeptidase, (b) glutamine cyclotransferase, and (c) pyroglutamine aminopeptidase, wherein said aminopeptidase catalyzes the removal of said A amino acid(s); said glutamine cyclotransferase catalyzes the conversion of said glutamine to pyroglutamine; and said pyroglutamine aminopeptidase catalyzes the removal of said pyroglutamine to produce said desired protein.

11. The process as defined in claim 10, wherein said aminoterminally extended protein is contacted simultaneously with said aminopeptidase, said glutamine cyclotransferase, and said pyroglutamine aminopeptidase.

12. The process as defined in claim 10, wherein said aminopeptidase is selected from the group consisting of dipeptidyl aminopeptidase, aeromonas aminopeptidase, aminopeptidase P, and proline iminopeptidase.

* * * * *

UNITED STATES PATENT AND TRADEMARK OFFICE
CERTIFICATE OF CORRECTION

PATENT NO. : 5,783,413
DATED : July 21, 1998
INVENTOR(S) : John Pedersen, Conni Lauritzen and Mads Thorup Madsen It is certified that error appears in the above-indentified patent and that said Letters Patent is hereby corrected as shown below:

In the Claims: Claim 2, line 2, please delete "(i)" after "simultaneously with."

Signed and Sealed this

Tenth Day of November 1998

*Attest:*

BRUCE LEHMAN

*Attesting Officer*     *Commissioner of Patents and Trademarks*